United States Patent [19]

Kreutner et al.

[11] Patent Number: 4,782,082
[45] Date of Patent: Nov. 1, 1988

[54] METHOD FOR TREATING ALLERGIC REACTIONS WITH FORSKOLIN

[75] Inventors: William Kreutner, West Caldwell; Michael J. Green, Skillman; Ho-Jane Shue, Pine Brook; Anil K. Saksena, Upper Montclair, all of N.J.

[73] Assignee: Schering Corporation, Kenilworth, N.J.

[21] Appl. No.: 894,380

[22] Filed: Aug. 7, 1986

Related U.S. Application Data

[60] Continuation of Ser. No. 698,955, Feb. 6, 1985, abandoned, which is a division of Ser. No. 542,825, Oct. 17, 1983, Pat. No. 4,517,200, which is a continuation-in-part of Ser. No. 453,436, Dec. 27, 1982, abandoned.

[51] Int. Cl.$^4$ ............................................. A61K 31/35
[52] U.S. Cl. .................................... 514/454; 514/455; 514/453; 514/430
[58] Field of Search .................... 549/389, 228, 90, 39, 549/22; 514/454, 455, 430, 453

[56] References Cited

U.S. PATENT DOCUMENTS 4,118,508 10/1978 Bhat et al. ........................ 514/455
4,134,986 1/1979 Bajwa et al. ..................... 514/455

OTHER PUBLICATIONS

Fieser and Fieser, Reagents for Organic Synthesis, John Wiley & Sons, New York, vol. 1, 1967, pp. 524–526, 1174.
Takeda et al., Chem. Abstr., 92, 177403j (1980).
Tandon et al., Ibid., 89, 163779n (1978).
Bajwa et al., Ibid., 89, 129755s (1978).
Hoechst, Ibid., 89, 24150n (1978).

*Primary Examiner*—Nicky Chan
*Attorney, Agent, or Firm*—Richard C. Billups; James R. Nelson; Stephen I. Miller

[57] ABSTRACT

Forskolin and its disclosed derivatives are useful as antiallergic agents. Certain of the derivatives are novel.

9 Claims, No Drawings

METHOD FOR TREATING ALLERGIC REACTIONS WITH FORSKOLIN

CROSS REFERENCE TO RELATED APPLICATION

This application is a file-wrapper-continuation of U.S. application Ser. No. 698,955, filed Feb. 6, 1985, now abandoned, which is a division of U.S. application Ser. No. 542,825, filed Oct. 17, 1983, now U.S. Pat. No. 4,517,200, which in turn is a continuation-in-part of U.S. application Ser. No. 453,436, filed Dec. 27, 1982, now abandoned.

BACKGROUND OF THE INVENTION

U.S. Pat. No. 4,118,508 describes a chemical compound, Coleforsin, which is said to possess hypotensive and positive inotropic effects.

U.S. Pat. No. 4,134,986 describes polyoxygenated labdane derivatives which are also said to possess hypotensive and positive inotropic activities.

The compound, Forskolin (7β-acetoxy-8,13-epoxy-1α,6β,9α-trihydroxylabd-14-en-11-one), is described in *Arzneimittel-Forsch./Drug Res.*, 31, (II), 1248 (1981) as an adenylatecyclase activator.

*J.C.S. Perkin I*, 767 (1982) describes certain synthetic modifications of Forskolin.

The present invention provides a method for treating allergic reactions in a mammal which utilizes Forskolin and certain of its derivatives.

SUMMARY OF THE INVENTION

The invention sought to be patented in its pharmaceutical method aspect is a method for treating allergic reactions in a mammal which comprises administering an antiallergic effective amount of a compound having structural formula I in combination with a pharmaceutically acceptable carrier to said mammal,

I wherein $R_1$ and $R_2$ may be the same or different and are =O, H, or $OR_{11}$ wherein $R_{11}$ is H, carboxylic acyl having from 1 to 6 carbon atoms or $$-CO-(CH_2)_m-\underset{}{\underset{}{\bigcirc}}-Y$$

wherein m is 0, 1, 2 or 3 and Y is hydrogen, halogen, alkyl having from 1 to 6 carbon atoms, alkoxy having from 1 to 6 carbon atoms, alkylthio having from 1 to 6 carbon atoms, OH, $CF_3$, $NO_2$, CN, phenyl, benzyl, phenoxy or $NR_aR_b$ wherein $R_a$ and $R_b$ are the same or different and are H or alkyl having from 1 to 6 carbon atoms;

$R_1$ and $R_2$ when taken together may form $$\begin{matrix} -O \\ -O \end{matrix} \diagdown\!\!\!\diagup \begin{matrix} R_{13} \\ R_{14} \end{matrix}$$

wherein $R_{13}$ and $R_{14}$ may be the same or different and are H, alkyl having from 1 to 6 carbon atoms, alkoxy having from 1 to 6 carbon atoms, alkenyl having from 2 to 6 carbon atoms, alkynyl having from 2 to 6 carbon atoms or $$-(CH_2)_m-\underset{}{\underset{}{\bigcirc}}-Y$$

wherein m and Y are defined above, or $R_2$ may be $SO_3OR'$ or $OR'$ wherein

R' is alkyl having from 1 to 6 carbon atoms; $R_3$ is hydrogen; alkyl having from 1 to 10 carbon atoms; $CH_2OH$; CHO; $CO_2R_{15}$ wherein $R_{15}$ is H or alkyl having from 1 to 6 carbon atoms;

—CH=$CR_{16}R_{17}$ wherein $R_{16}$ is H, halogen, alkyl having from 1 to 6 carbon atoms, $$CN, \overset{O}{\underset{\|}{C}}(O)_nR_c$$

wherein n is 0 or 1 and $R_c$ is H, alkyl having from 1 to 6 carbon atoms, phenyl or benzyl, $CHOHR_c$ or $C(OR_d)_2R_c$ wherein $R_c$ is defined above and $R_d$ is alkyl having from 1 to 6 carbon atoms, $R_{17}$ is H, alkyl having from 1 to 6 carbon atoms, alkoxy having from 1 to 6 carbon atoms, benzyl, phenyl or halogen;

—C≡C—$R_{18}$ wherein $R_{18}$ is H, alkyl having from 1 to 12 carbon atoms, alkoxy having from 1 to 6 carbon atoms, $$-CH_2-\underset{}{\underset{}{\bigcirc}}-Y ,$$

$CO_2Rc$ or $$\underset{}{\underset{}{\bigcirc}}-Y$$

wherein Y and Rc are defined above;
—CHOH—C≡C—$R_{19}$ wherein $R_{19}$ is H, alkyl of from 1 to 6 carbon atoms, phenyl or benzyl;
—CH=C=$CHR_{19}$ wherein $R_{19}$ is defined above;
—CH=N—$OR_{19}$ wherein $R_{19}$ is defined above;

$$-CH\diagup\!\!\!\diagdown\begin{matrix} Z \\ \diagdown\!\!\!\diagup \end{matrix}\begin{matrix} R_{16} \\ R_{19} \end{matrix}$$

wherein Z is O or S, and $R_{16}$ and $R_{19}$ are defined above;

—$CH(ZR_{20})_2$ wherein Z is defined above and $R_{20}$ is alkyl having from 1 to 6 carbon atoms, phenyl, benzyl or the two groups $R_{20}$ may together form —$(CH_2)_p$— wherein p is 2 or 3;

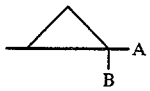

wherein A and B are H, halogen, alkyl having from 1 to 6 carbon atoms, phenyl, benzyl or

wherein n and $R_c$ are defined above;
—CH=N—NDE wherein D and E are H, alkyl having from 1 to 6 carbon atoms, benzyl, phenyl, COG, $SO_2G$, or $CO_2G$ wherein G is alkyl having from 1 to 6 carbon atoms, benzyl or phenyl;
$R_4$ is H or OH;
$R_5$ is OH; or when
$R_4$ and $R_5$ are taken together they may form

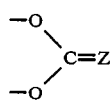

wherein z is defined above;
a is an optional bond which may be located in either the 5,6 or 6,7 position;
b is an optional bond, when present Q and $R_3$ are missing;
X is O or K/OR" wherein R" is hydrogen, carboxylic acyl having from 1 to 6 carbon atoms or trifluoroacetyl; and
Q is hydrogen, chlorine or bromine.
The preferred values for the above-defined substituents are as follows:
$R_1$ and $R_2$ may be the same or different and are hydrogen or $OR_{11}$ wherein $R_{11}$ is defined hereinabove and Y is hydrogen;
$R_3$ is hydrogen, alkyl having from 1 to 6 carbon atoms, —CH=CHR$_{301}$ or —C≡CR$_{301}$ [wherein $R_{301}$ is hydrogen, alkyl having from 1 to 6 carbon atoms, phenyl, benzyl or $CO_2R_c$];
$R_4$ is H or OH;
$R_5$ is OH;
a is either not present or is located in the 5,6 position in which instance $R_1$ is preferably H and $R_2$ is preferably $OR_{11}$ wherein $R_{11}$ is defined hereinabove;
Y is hydrogen;
X is O or H/OH; and
Q is hydrogen or chlorine.
The invention sought to be patented in its first chemical compound aspect is a chemical compound having structural formula I as defined above wherein
$R_4$ is H; provided that 8,13-epoxy-1α6β,7β,11α-tetrahydroxylabd-14-ene is excluded.
The invention sought to be patented in its second chemical compound aspect is a chemical compound having structural formula I as defined above provided that when $R_4$ is OH then $R_3$ is not CH=CH$_2$, $C_2H_5$, CHO or

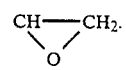

The invention sought to be patented in its third chemical compound aspect is a chemical compound having structural formula I as defined above wherein
a is a 5,6 double bond;
$R_1$ is hydrogen; and
$R_5$ is hydroxy.
The invention sought to be patented in its fourth chemical compound aspect is a chemical compound having structural formula I as defined above wherein
a is a 5,6 double bond;
X is O or α-H/β-OH;
Q is H or Cl;
$R_1$ is H;
$R_2$ is $OR_{11}$;
$R_3$ is H, $CH_3$, $CH_2H_5$ or CH=CH$_2$;
$R_4$ is H or OH; and
$R_5$ is OH.
Preferred chemical species of the invention are as follows:
8,13-epoxy-1α,6β,7β-trihydroxy-labd-14-en-11-one 7-acetate;
8,13-epoxy-1α,7β,9β-trihydroxy-labd-5(6)-ene-11-one 7-acetate;
8,13-epoxy-1α,6β,7β-trihydroxy-labd-14-en-11-one 6-acetate;
8,13-epoxy-1α,7β,9β-trihydroxy-labd-5(6),14-diene-11-one 7-acetate;
8,13-epoxy-1α,6β,7β-trihydroxy-labd-14-en-11-one;
8,13-epoxy-1α,6β,7β,11β-tetrahydroxy-labd-14-ene;
8,13-epoxy-1α,6β,7β,11β-tetrahydroxy-labd-14-ene-7-acetate;
12-chloro-8,13-epoxy-1α,7β-dihydroxy-labda-5(6), 14-dien-11-one 7-acetate;
15-nor-8,13-epoxy-1α,6β,7β,9α-tetrahydroxy-labdan-11-one;
15-nor-8,13-epoxy-1α,6β,7β,9α-tetrahydroxy-labdan-11-one 7-acetate;
8,13-epoxy-1α,7β,9α-trihydroxy-labd-5(6),14-diene 7-propionate.

The invention sought to be patented in a pharmaceutical composition aspect is a composition useful for treating allergic reactions in a mammal which comprises a compound having structural formula I in combination with a pharmaceutically acceptable carrier.

DESCRIPTION OF THE INVENTION

The compounds utilized in the method of the invention may be prepared by standard procedures. A convenient starting material for preparing these compounds is 7β-acetoxy-8,13-epoxy-1α,6β,9α-trihydroxylabd-14-en-11-one, Forskolin, [*J.C.S. Perkin* I, 767 (1982)].

Those skilled in the art will recognize that in order to carry out a particular desired synthetic conversion it may be necessary to first protect other reactive sites which may be present in a molecule. Such protection is preferably accomplished by first forming a derivative at the site to be protected which derivative may be readily re-converted to the original functionality, if desired, after the particular synthetic conversion has been carried out. Examples of such protective conversions are esterification of alcohols and ketalization of ketones.

Other such conversions will suggest themselves to those skilled in the art. Because such techniques are recognized as within the skill of the art, they are not included in the following description of the preparation of the compounds utilized in the method of the invention.

Compounds wherein $R_1$ is $=O$ may be prepared by oxidizing a corresponding compound wherein $R_1$ is OH. Compounds wherein $R_1$ is $OR_{11}$ may be prepared by acylation of a compound wherein $R_1$ is OH. Compounds wherein $R_1$ is H may be prepared by reduction of a compound wherein $R_1$ is $=O$.

Compounds having $R_2$ substituents as described herein may be prepared substantially as described hereinabove for a corresponding $R_1$ substituent.

Compounds wherein $R_1$ and $R_2$ together form

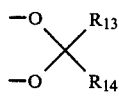

may be prepared by reacting a corresponding compound wherein $R_1=R_2=$ OH with an aldehyde or ketone. Such reactions are generally carried out using conditions whereby the reaction-produced water may be continuously removed.

Compounds having the additional bond, a, may be produced for example by dehydration of a suitable compound wherein $R_1$ and/or $R_2$ are hydroxy.

Compounds wherein $R_3$ is CHO may be prepared from the starting compound (which has a vinyl group at this position) by ozonolysis. Compounds wherein $R_3$ is $CH_2OH$ or $CO_2R_{15}$ may be prepared respectively by reducing or oxidizing the corresponding aldehyde. The carboxylic acid so produced ($R_{15}=H$), thereafter may be esterified if desired. Compounds wherein $R_3$ is $-CH=CR_{16}R_{17}$ may be prepared by treating a compound wherein $R_3$ is CHO with a Wittig reagent, $\phi_3P=CR_{16}R_{17}$. Certain of the substituents, $R_{16}$ and $R_{17}$ may be modified or interconverted subsequent to the Wittig reaction, when desired. Compounds wherein $R_3$ is $-C\equiv C-R_{18}$ may be prepared by treating a compound wherein $R_3$ is CHO with a reagent $\phi_3P+CHBrR_{18}$ to produce a bromine containing intermediate which may be dehydrobrominated to produce the desired product. Compounds wherein $R_3$ is $C\equiv CH$ may be prepared by the addition of bromine to a corresponding compound wherein $R_3$ is $-CH=CH_2$ followed by didehydrobromination. Compounds wherein $R_3$ is $-CHOH-C\equiv C-R_{19}$ may be prepared from a compound wherein $R_3$ is CHO by treatment with a reagent, $MC\equiv C-R_{19}$, wherein M is a suitable metal such as lithium. Compounds wherein $R_3$ is $-CH=C=CHR_{19}$ may be prepared from a corresponding compound wherein $R_3$ is $-CHOH-C\equiv C-R_{19}$ by first esterifying the hydroxyl group and treating the so obtained ester with aluminum chloride. Compounds wherein $R_3$ is $-CH=N-OR_{19}$ may be prepared from a compound wherein $R_3$ is CHO by treatment with a reagent of the formula $H_2N-OR_{19}$. Compounds wherein $R_3$ is

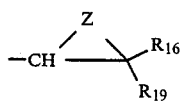

may be prepared from a compound wherein $R_3$ is $-CH=CR_{16}R_{19}$ by treatment with a peracid such as m-chloroperbenzoic acid to produce compounds wherein Z is oxygen, these compounds may be converted to corresponding compounds wherein Z is sulfur by treatment with potassium isothiocyanate. Compounds wherein $R_3$ is $-CH(ZR_{20})_2$ may be prepared from a compound wherein $R_3$ is CHO by treatment with an alcohol or thiol using standard procedures. Compounds wherein $R_3$ is

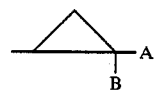

may be prepared by the addition of a dihalocarbene to a compound wherein $R_3$ is $-CH=CH_2$ or by the addition of a methylene carbene to a compound wherein $R_3$ is $-CH=CAB$. Compounds wherein $R_3$ is $-CH=N-NDE$ may be prepared by treating a compound wherein $R_3$ is CHO with a compound having the formula $H_2N-NDE$ using standard procedures.

Compounds wherein $R_4$ is hydrogen may be prepared, for example, by first forming an internal 1,9-carbonate or thiocarbonate ester utilizing a starting material wherein $R_4=R_5=OH$. Convenient reagents for performing these conversions are carbonyl diimidazole or thiocarbonyl diimidazole, respectively. The so produced esters upon treatment with zinc in acetic acid produce the compound wherein $R_4$ is hydrogen and $R_5$ is hydroxy.

The compounds of this invention wherein X is H/OH may be prepared by a suitable reduction of a compound wherein X is $=O$.

When utilized herein the following terms will have the indicated meanings unless otherwise specified:

alkyl—straight and branched carbon chains having from 1 to 6 carbon atoms;

alkoxy and alkylthio—comprised of straight and branched carbon chains having from 1 to 6 carbon atoms which are singly bonded respectively to an oxygen or a sulfur atom;

halogen—fluorine, chlorine, bromine and iodine;

carboxylic acyl—the acyl portion derived from a straight or branched chain alkanoic acid having from 1 to 6 carbon atoms;

alkenyl—straight or branched carbon chains comprising one double bond and having from 2 to 6 carbon atoms;

alkynyl—straight and branched carbon chains comprising one triple bond and having from 2 to 6 carbon atoms.

The following numbering system is utilized herein for the Forskolin skeleton unless specified otherwise:

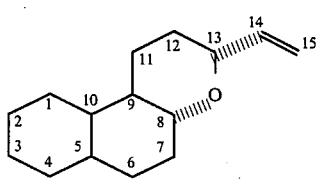

a dashed line (----) indicates that the substituent is projected below the plane of the paper and is denoted as α;

a heavy line (━) indicates that the substituent is projected above the plane of the paper and is denoted as β.

The active compounds utilized in the method of this invention may exist as solvates, for example as hydrates.

Certain compounds of the invention may exist as optical and/or geometric isomers. For example, substituents at positions 6, 7 and 11 of the forskolin skeleton as well as certain $R_3$ substituents may exist in isomeric forms. In addition, when $R_3$ is hydrogen, both epimers at the C-13 carbon atom are included. The invention contemplates all isomers both in pure form and in admixture.

The compounds used in the methods of this invention can be used to treat allergy caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy method of this invention is identified by tests which measure a compound's inhibition of anaphylatic bronchospasm in sensitized guinea pigs having antigen induced bronchoconstriction. For example, the compound 7β-acetoxy-8,13-epoxy-1α,6β,9α-trihydroxy-labd-14-en-11-one was found to inhibit anaphylactic bronchospams in such test procedure when given at a dose of 1–3 mg/kg intravenously. Said compound was also found to inhibit allergen-induced histamine release from guinea pig and human sensitized tissue. The compounds are effective non-adrenergic, non-anticholinergic, antianaphylactic and bronchodilator agents. When administered orally they are active at doses of from about 0.2 to 20 mg/kg of body weight; when administered parenterally, e.g., intravenously, the compounds are active at dosages of from about 0.1 to 3 mg/kg body weight; when administered by inhalation (aerosol or nebulizer) the compounds are active at dosages of about 0.1 to 10 mg per puff, one to four puffs may be taken every 4 hours.

The amount, route and frequency of administration of the compounds will be regulated accordingly to the judgement of the attending clinician considering such factors as age, condition and size of the patient as well as severity of the disease being treated. A typical recommended dosage regimen is oral administration of from 10 to 3000 mg/day, preferably 100 to 1000 mg/day, in two to four divided doses to achieve relief of the symptoms.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e. sterile solutions or suspensions are also made by conventional means. Inhalation administration can be in the form of a nasal or oral spray. Insufflation is also contemplated. Topical dosage forms can be creams, ointments, lotions and the like. Other dosage forms which can be utilized are transdermal devices and suppositories.

The following test procedure was utilized to assess the usefulness of the compounds of the invention for inhibiting antigen induced anaphylactic bronchospasm.

Male Hartley guinea pigs were sensitized with 5 mg ovalbumin injected intraperitoneally (i.p.) and 5 mg injected subcutaneously (s.c.) in 1 ml saline on day 1 and 5 mg ovalbumin injected i.p. on day 4. The sensitized animals were used 3-4 weeks later.

To measure anaphylactic bronchospasm, sensitized guinea pigs were fasted overnight and the following morning anesthetized with 0.9 ml/kg i.p. of dialurethane (0.1 gm/ml diallylbarbituric acid, 0.4 gm/ml ethylurea and 0.4 gm/ml urethane). The trachea and jugular vein were cannulated and the animals were ventilated by a Harvard rodent respirator at 50 strokes/min with a stroke volume of 5 ml. A side arm to the tracheal cannula was connected to a Harvard pressure transducer to obtain an continuous measure of intratracheal pressure which was recorded on a Harvard polygraph. The recorder was calibrated so that a pressure of 50 mm Hg produced a 25 mm pen deflection. An increase in intratracheal pressure was taken as a measure of bronchoconstriction.

Each guinea pig was injected intravenously (i.v.) with 1 mg/kg dl-propranolol (HCl salt), 5 mg/kg indomethacin and 2 mg/kg mepyramine (maleate salt) given together in a volume of 1 ml/kg. Fifteen minutes later, the animals were challenged with antigen (0.5 per cent ovalbumin) delivered as an aerosol generated from a DeVilbiss Model 65 ultrasonic nebulizer and delivered through the tracheal cannula for 30 seconds. Bronchoconstriction was measured as the peak increase in intratracheal pressure occurring within 15 minutes after antigen challenge.

Bronchoconstriction was studied in four guinea pigs at a time. The effect of test compound given i.v. on anaphylactic bronchospasm is expressed as per cent reversal of the peak increase in intratracheal pressure.

Results from the above procedure for representative compounds of the invention are given below.

| Forskolin derivative | Percentage reversal at dose (mg/kg) |
| --- | --- |
| 8,13-Epoxy-1α,6β,7β,9α-tetrahydroxy-labd-14-en-11-one 7-acetate | 70 (1)<br>65 (0.3) |
| (Forskolin) | 43 (0.1) |
| 8,13-Epoxy-1α,6β,7β,9α-tetrahydroxy-labd-14-en-11-one | 69 (1) |
| 8,13-Epoxy-1α,6β,7β,9α-tetrahydroxy-labd-14-en-11-one 6-acetate | 70 (1) |
| 8,13-Epoxy-1α,6β,7β,9α-tetrahydroxy-labdan-11-one 7-acetate | 30 (1) |
| 8,13-Epoxy-1α,6β,7β,9α,11β-pentahydroxy-labd-14-ene 7-acetate | 33 (1) |
| 8,13-Epoxy-1α,6β,7β,9α,11β-pentahydroxy-labd-14-ene | 25 (1) |

The following examples illustrate the preparation of representative compounds of the invention.

EXAMPLE I 8,13-Epoxy-1α,6β,7β,9α-tetrahydroxylabdan-11-one 7-acetate

Forskolin (30 mg) in MeOH (9 ml) with 10% Pd/C was hydrogenated at room temperature and atmospheric pressure for 2 hours. The catalyst was filtered off, and the solvent evaporated. Recrystallization from ether/hexane gave product, (16 mg) m.p. 242°-244° C.

EXAMPLE II 8,13-Epoxy-1α,6β,7β,9α-tetrahydroxylabd-14-en-11-one 7-acetate 1,9-thiocarbonate Forskolin (100 mg) was stirred with carbonyl diimidazole (130 mg) in $CH_2Cl_2$ (6 ml) at room temperature for 6 days. The solvent was evaporated and the residue chromotographed on a column of silica gel (10 g). Elution with 10% EtOAc/CHCl$_3$ gave product which was crystallized from ether/hexane (68 mg) m.p. 241°–243° C.

EXAMPLE III 8,13-Epoxy-1α,6β,7β-trihydroxylabd-14-en-11-one 7-acetate

The thiocarbonate of forskolin (0.23 g) from Example II in AcOH (11.5 ml) was treated with Zn powder (0.66 g) and was heated to 120° C. for 20 minutes. The zinc was filtered off hot, the filtrate poured into H$_2$O (100 ml) and neutralized with NaOH. The product was extracted into ethyl acetate and chromotographed on a column of silica gel eluting with 10% EtOAc/CHCl$_3$ to give product which crystallized from acetone-hexane; (93 mg) m.p. 157.5°–160° C.

EXAMPLE IV 8,13-Epoxy-1α,7β,9α-trihydroxylabd-5(6)-en-11-one 7-acetate

Forskolin (1 g), benzyl bromide (0.82 ml), potassium iodide (1 g) and potassium carbonate (5 g) in 30 ml dry acetone was heated to 60° C. for 18 hours. After cooling the precipitate was filtered off, the filtrate was evaporated and the residue was separated on a column of silica gel (100 g) eluting with 5% EtOAc/CHCl$_3$ to give 1α-benzylforskolin (0.15 g). 80 mg of this material was treated with thionyl chloride (0.08 ml) in pyridine (0.8 ml) for 4 hours at 0° C. The reaction was poured into water and the product was isolated by extraction with ethyl acetate. This product was hydrogenated (PtO$_2$ 0.5 g, EtOAc 15 ml) for 24 hours at room temperature after which it was purified on a column of silica gel eluting with 20% EtOAc/hexane to give product crystallized from acetane hexane (19 mg).

EXAMPLE V 8,13-Epoxy-1α,6β,7β-trihydroxylabd-14-en-11-one

9-Deoxyforskolin (0.44 g) prepared in Example III in methyl alcohol (21 ml) was treated with 5.28 ml of a 1.66% NaOH aqueous solution for 17 hours at room temperature. The resulting solution was neutralized with 2N HCl, the methanol was removed under reduced pressure and the product was taken into ethyl acetate. The organic layer was washed with water, dried (MgSO$_4$) and the solvent was evaporated to a residue which was purified on a column of silica gel (eluting with 40% EtOAc/hexane) to give product 0.15 g.

EXAMPLE VI

A. 8,13-Epoxy-1α,6β,7β-trihydroxylabd-14-en-11-one 7-benzoate

The product from Example V (50 mg) was treated in pyridine (0.5 ml) at 0° C. with benzoyl chloride (0.018 ml) for 50 minutes. 2NHCl was added and then water; the product was isolated and purified on a column of silica gel eluting with 25% EtOAc/hexane. Crystallization from acetone-hexane gave product 33 mg m.p. 164.5° C.

B. 8,13-Epoxy-1α,6β,7β-trihydroxylabd-14-en-11- one 7-pentanoate

In a similar manner to Example VI A but substituting valeroyl chloride for benzoyl chloride, the product was obtained, m.p. 98°–100 ° C.

C. 8,13-Epoxy-1α,6β,7β-trihydroxylabd-14-en-11-one 7-(2-methylpropanoate)

In a similar manner to Example VI A but substituting 2-methylpropanoyl chloride for benzoyl chloride, the product was obtained, m.p. 145.5°–147.5° C.

EXAMPLE VII

Forskolin 1,9-carbonate

A stirred and cooled (ice bath) solution of Forskolin (1 g) in dry methylene chloride (10 ml) and pyridine (3 ml) was treated with a solution of phosgene in methylene chloride (3 ml; approx. 13% phosgene by weight). After 45 minutes the starting material was all consumed. Methylene chloride and pyridine were removed in vacuo and the residue was distributed between methylene chloride (25 ml) and water (10 ml). The organic phase was separated and the aqueous phase extracted twice with methylene chloride. The combined organic extracts were dried (Na$_2$SO$_4$) and evaporated to dryness to provide a crystalline solid, 1.29 gms. A 100 mg. portion of this product was recrystallized from ethyl acetate/n-hexane, m.p. 121°–123° C.

EXAMPLE VIII 14,15-Dinor-8,13-epoxy-13-formyl-1α,6β,7β,9α-tetrahydroxylabdan-11-one 1,9-carbonate A solution of Forskolin 1,9-carbonate (0.2 g) prepared as in Example VII in methylene chloride (4 ml) and methanol (3 ml) was cooled in acetone/dry ice bath. Ozone/oxygen was passed through this solution until excess ozone (indicated by blue coloration) was present (approx. 5–7 minutes). Excess ozone was driven off by passing argon through the solution and 0.5 ml dimethylsulfide was added. The reaction mixture was gradually allowed to warm to room temperature and after stirring 2 hours, evaporated to dryness in vacuo. The residue was dissolved in methylene chloride (15 ml) and washed with water. The methylene chloride solution was dried (Na$_2$SO$_4$) and evaporated to dryness to yield a crystalline product nearly homogenous by TLC. Yield: 0.190 g. A 20 mg. portion was recrystallized from ethyl acetate/n-hexane, m.p. 237°–238° C.

EXAMPLE IX

15-Nor-8,13-epoxy-1α,6β,7β,9β-tetrahydroxy-14-hydroxyiminolabdan-11-one 7-acetate 1,9-carbonate A solution of the aldehyde (0.4 g) prepared as in Example VIII in dry pyridine (5 ml) was cooled (ice bath) and treated with solid NH$_2$OH.HCl (0.07 g) with stirring. After approximately 2 hours the reaction mixture was diluted with methylene chloride (25 ml) and treated with dilute H$_2$SO$_4$ (0.1N) until the aqueous phase was acidic. The methylene chloride layer was separated, and the aqueous phase was extracted once with methylene chloride. The combined methylene chloride extracts were washed once with water, dried (Na$_2$SO$_4$) and evaporated to dryness to provide a crystalline TLC homogenous product. Yield: 0.38 g. A small portion of this product (30 mg.) was recrystallized from chloroform to provide colorless cubes, m.p. 277°–280° C.

EXAMPLE X 14,-E and Z-8,13-Epoxy-1α,6β,7β,9α-tetrahydroxylabd-14-en-11-one 7-acetate 1,9-carbonate 15-methylcarboxylate A solution of the aldehyde (0.1 g) as prepared in Example VIII in methylene chloride (5 ml) was treated with the phosphorane (Ph$_3$P=CH.COOMe) (0.085 g; ca. 1.1 equiv.) and the reaction mixture refluxed for 2 hours. TLC showed a two-component mixture. Refluxing for an additional 2 hours did not change the product ratios by TLC. The methylene chloride was replaced by benzene (4 ml), additional phosphorane (0.04 g) was added and the reaction mixture again refluxed for 1 hour. The benzene was evaporated to dryness in vacuo and the residue subjected to chromatography on two 1 mm thick silica gel plates using 40% acetone/n-hexane as eluent:

| LESS POLAR COMPONENT A (Z-isomer) | 0.08 g. crystals m.p. 120–121° C. |
|---|---|
| MORE POLAR COMPONENT B (E-isomer) | 0.04 g. crystals m.p. 214–216° C. |

EXAMPLE XI 8,13-Epoxy-1α,7β,9α-trihydroxylabda-5(6),14-diene-11-one 7-acetate 1,9-carbonate To a stirred solution of forskolin 1,9-carbonate (0.87 g,) from Example VII in dry CH$_2$Cl$_2$ (17.4 ml) was added diethylaminosulfurtrifluoride (0.5 ml) under a nitrogen atmosphere at 0° C. After stirring for 15 minutes, another portion of diethylaminosulfurtrifluoride (0.5 ml) was added and stirred for a further 30 minutes. EtOAc (200 ml) was added to the mixture and then washed immediately with saturated NaHCO$_3$ solution and water. The organic fraction was dried (MgSO$_4$) and evaporated in vacuo to dryness to yield a white solid, 0.79 g (95%). A portion of product was crystallized from EtOAc/hexane to give product m.p. 164°–166° C.

EXAMPLE XII (a) 8,13-Epoxy-1α,7β,9α-trihydroxy-labda-5(6),14-diene-11-one and (b) 8,13-Epoxy-1α,7β,9β-trihydroxy-labd-5(6),14-diene-11-one 7 acetate A mixture of 8,13-epoxy-1α,7β,9α-trihydroxy-labd-5(6),14-diene-11-one 7-acetate 1,9-carbonate (0.78 g), prepared as in Example XI, MeOH (40 ml) and NaOH solution (1.66% in H$_2$O, 5 ml) was stirred at room temperature for 3.5 hours. An additional NaOH solution (1.66% NaOH in H$_2$O, 5 ml) was added and stirred for a further 30 minutes. The mixture was neutralized with a few drops of HCl (2N) and the solution was evaporated in vacuo. The residue was redissolved in EtOAc and washed with brine, dried (MgSO$_4$) and concentrated under reduced pressure to give a white solid, 0.64 g. Column chromatography (100 g silica gel, 40% EtOAc/CHCl$_3$) afforded 8,13-epoxy-1α,7β,9α-trihydroxy-labda-5(6),14-diene-11-one 0.51 g (78%) which was crystallized from acetone/hexane, m.p. 179°–181° C. and 8,13-epoxy-1α,7β,9α-trihydroxy-labd-5(6),14-diene-11-one 7-acetate 0.13 g (18%) which was crystallized from ethylacetate/hexane, m.p. 119°–121° C.

EXAMPLE XIII 8,13-Epoxy-1α,7β,9α-trihydroxy labda-5(6), 14-diene-11-one 7-propionate To a cooled solution of 8,13-epoxy-1α,7β,9α-trihydroxy-labd-5(6),14-diene-11-one (40 mg,) prepared as in Example XII in distilled pyridine (0.4 ml) was added propionic anhydride (0.2 ml) at 0° C. (ice-water bath). The mixture was stirred at 0° C. for 2.5 hours then at room temperature for 2 hours. The mixture was diluted with EtOAc (200 ml) and washed with 1N HCl, H$_2$O and dried (MgSO$_4$). The solvent was evaporated in vacuo to a residue which was purified on thin layer chromatography plate (silica plates, 1 mm, 40% EtOAc/hexane) to give product 26 mg (0.64 mmol, 56%). Crystallization from petroleum ether gave product 20 mg. m.p. 109.5° C.–111° C.

EXAMPLE XIV 8,13-Epoxy-1α,7β,9α-trihydroxy-labda-5(6), 14-diene-11-one 7-methylether To a mixture of sodium hydride (60%, 5.7 mg) in THF (freshly distilled, 0.3 ml) was added CH$_3$I (0.009 ml, 0.14 mmol) and the product from Example XIIa (25 mg, 0.07 mmol) in 0.3 ml of THF under a nitrogen atmosphere. The mixture was heated at 60° C. for 30 minutes and quenched with a few drops of 1N HCl. Solvent was evaporated and the residue was separated on thin layer chromatography plates (silica gel, 40% EtOAc/Hexane) to give product 12 mg, (0.033 mmol, 46%) which crystallized from EtOAc/Hexane to give product 10 mg m.p. 133°–135° C.

EXAMPLE XV 8,13-Epoxy-1α,6β,7α-trihydroxy-labda-14-en-11-one 7-methanesulfonate A mixture of the product from Example V (50 mg) in pyridine (0.5 ml) and CH$_3$SO$_2$Cl (25 μl) was stirred at room temperature for 1 hour. EtOAc (200 ml) was added to the mixture and washed immediately with 1N HCl and then with H$_2$O. The organic phase was dried (MgSO$_4$) and evaporated in vacuo to give a residue 54 mg. Purification on silica gel thin layer chromatography plates, (10% EtOAc/CHCl$_3$) yielded product 33 mg (0.073 mmol, 54%) m.p. 90°–92° C.

EXAMPLE XVI 8,13-Epoxy-1α,7β,9α,11β-tetrahydroxy labda-5(6),14-diene

A mixture of the product from Example VII (forskolin 1,9-carbonate) (90 mg, 0.215 mmol) in THF (1 ml) ethylether (3.6 ml) and lithium aluminum hydride (45 mg, 1.18 mmol) was heated at 40° C. under a nitrogen atmosphere for 1 hour. To the cooled mixture (in ice-water bath) was added 50 ml Et$_2$O and 0.2 ml of saturated Na$_2$SO$_4$ solution and stirred for 0.5 hour. The white precipitate was filtered off and washed with Et$_2$O (50 ml). The filtrate was evaporated under reduced pressure to give a white residue 80 mg. This residue was purified on silica gel thin layer chromatography plates, (40% EtOAc/Hexane) to yield product 28 mg (0.079 mmol, 37%). Crystallization from EtOAc/Hexane gave product 22 mg. m.p. 120°–126° C.

EXAMPLE XVII 8,13-Epoxy-1α,6β,7β,11β-tetrahydroxy labd-14-ene

A mixture of product from Example III (9-deoxyforskolin) (15 mg, 0.14 mmol) in Et$_2$O (3.0 ml) and lithium aluminum hydride (25 mg, 0.66 mmol) was heated to 40° C. under a nitrogen atmosphere for 1.5 hours. The mixture was diluted with Et$_2$O (50 ml) and cooled in ice-water bath. To the cooled mixture was dropwise added saturated Na$_2$SO$_4$/H$_2$O solution (1 ml) and stirred for 30 minutes. The white precipitate was filtered off and washed with Et$_2$O (50 ml). The organic solution was concentrated in vacuo to give a residue 44 mg. Purification of the residue on alumina TLC plate (250μ, 5% EtOAc-1% MeOH -94% CHCl$_3$) yielded product 23 mg (0.5 mmol, 46%) which crystallized from EtOAc/hexane, 21 mg m.p. 189°–190° C. cl EXAMPLE XVIII 8,13-Epoxy-1α,6β7β,11β-tetrahydroxy labd-14-ene 7-acetate To a solution of crude product (94 mg, 0.265 mmol), prepared as in Example XVII, in pyridine (0.94 ml) and CH$_2$Cl$_2$ (0.14 ml) was added acetic anhydride (0.135 ml, 1.32 mmol). The mixture was stirred at room temperature overnight, H$_2$O (100 ml) was added to quench the reaction and product was extracted with EtOAc. The organic layer was washed with 1N HCl, H$_2$O and dried (MgSO$_4$). The solvent was evaporated in vacuo to give a residue. Column chromatography on silica gel, (2% MeOH/CHCl$_3$) gave product 49 mg (47%) m.p. 132°–136° C.

EXAMPLE XIX

15-Nor-1,13-epoxy-1α,6β,7β,9α-tetrahydroxy -14-dithioethylene-labdan-11-one-7-acetate; 1,9-carbonate A solution of the product from Example VIII (100 mg) in 5 ml dry CH$_2$Cl$_2$ containing 40 μl ethanedithiol was cooled to −78° C. under N$_2$. To this was added 60 l of BF$_3$. Et$_2$O and the reaction was allowed to stir at this temperature for 1 hour. The reaction mixture was quenched with water and extracted with CH$_2$Cl$_2$. The organic extract was washed with dilute NH$_4$OH solution dried (Na$_2$SO$_4$) and the solvent removed, to give the product (purified by preparative TLC eluting with 50% EtOAc/hexane) 80 mg, m.p. 285°–287° C. (d).

EXAMPLE XX

15-Nor-8,13-epoxy-1α,6β,7β,9α-tetrahydroxy-14-dithioethylene-labdan-11-one

A solution of the product from Example XIX (32.1 mg) in methanol (6.0 ml) was treated with 10% NaOH (1.5 ml). The reaction was allowed to stir for 16 hours. Oxalic acid (112.5 mg) was added and the product was extracted with CH$_2$Cl$_2$, separated and dried. Solvent removed to give the product 30 mg.

EXAMPLE XXI

15-Nor-8,13-epoxy-1α,6β,7β,9α-tetrahydroxy-14-dithioethylene-labdan-11-one-7-acetate The product from the Example XX (69.5 mg) was acylated in dry pyridine (0.7 ml), with Ac$_2$O (73.4 l) and dry CH$_2$Cl$_2$ (0.7 ml) in a similar manner as in Example XXIII. Purification by preparative TLC, eluting with EtOAc/MeOH/CHCl$_3$ (5:1:94), afforded product 38.4 mg white solids m.p. 216°–218° C. (d).

EXAMPLE XXII

15-Nor-8,13-epoxy-1α,6β,7β,9α-tetrahydroxy-labdan-11-one

The product from Example XXI (165 mg) was desulfurized with 9 ml Ra/Ni suspension in 16 ml ethanol. The mixture was allowed to stir at room temperature for 16 hours. After filtration and washing with ethanol, the solvent was removed to give 112 mg. of the product. Recrystallization from methanol afforded white crystals of the product m.p. 191°–192° C.

EXAMPLE XXIII

15-Nor-8,13-epoxy-1α,6β,7β,9α-tetrahydroxy labdan-11-one-7-acetate

The product from Example XXII (91 mg) was dissolved in 0.8 ml dry pyridine and was treated with a solution of acetic anhydride (0.093 ml) in dry methylene chloride (0.8 ml). The reaction mixture was allowed to stir at room temperature under N$_2$ for 16 hours. The mixture was distributed between water and methylene chloride, the organic layer was washed with dilute HCl, dried and the solvent removed to give the product 87.4 mg. This crude product, purified by preparative TLC, eluting with 2% MeOH/CHCl$_3$, gave 40 mg crystalline product m.p. 274°14 276° C.

EXAMPLE XXIV 14,15-Dinor-13-cyclopropyl-8,13-epoxy-1α,6β,7β,9α-tetrahydroxy-labadan-11-one-7-acetate A solution of forskolin (100 mg) in dry THF (1.0 ml) was treated with diazomethane in ether solution (3 ml) at 0° C. A small amount of Pd(OAc)$_2$ was added and the reaction mixture was stirred at this temperature for 15 minutes. The product was isolated and purified by preparative TLC, eluting with 5:1:94 ratio of EtOAc:MeOH:CHCl$_3$. Crystalliation from CHCl$_3$ gave the product 65 mg, white crystals m.p. 253°–256° C.

EXAMPLE XXV 14,15-Dinor-13-cyclopropyl-8,13-epoxy-1α,6β,7β-hydroxy-labadan-11-one-7-acetate 9-Deoxyforskolin (100 mg) prepared as in Example III was cyclopropanated in a similar manner as in Example XXIV. The product was purified on a column of silica gel, eluting with 20% EtOAc/CHCl$_3$, and was further purified by preparative TLC, eluting with 30% EtOAc/CHCl$_3$, to give the product 53.2 mg. Crystallization from diisopropylether gave m.p. 205°–205° C.

EXAMPLE XXVI 8,13-Epoxy-1α,6β,7β-trihydroxy-labd-14-en-11-one 6-acetate

A mixture of product from Example II (500 mg, 1.4 mmol), acetic acid (25 ml) and Zn powder (1.44 g) was heated at 120° C. under a nitrogen atmosphere. After 30 minutes, another portion of Zn powder (1.44 g) was added and the mixture heated for a further 30 minutes. After cooling, the zinc was filtered off and the filtrate was concentrated in vacuo to a residue which was redissolved in EtOAc (300 ml), washed with water and dried (MgSO$_4$). The organic solvent was evaporated in vacuo and the residue was chromatographed on a column of silica gel eluting with 10% EtoAc/CHCl$_3$ to give 9-desoxy forskolin 308 mg and product 40 mg. A 30 mg portion of the product was crystallized from acetone-hexane to give m.p. 190°–192° C.

EXAMPLE XXVII 8,13-Epoxy-1α,7β-dihydroxy-labda-5(6),14-diene-11-one 7-acetate To a solution of the product from Example XI (70 mg 0.167 mmol) in acetic acid (3.5 ml) was added Zn powder (0.21 g). The mixture was heated to 120° C. under a nitrogen atmosphere for 1.5 hours. EtOAc (100 ml) was added and the Zn was filtered off. The filtrate was poured into H$_2$O (50 ml), neutralized with NaOH and the product was extracted into ethyl acetate. Chromatograph on a column of silica gel eluting with 30% EtOAc/hexane gave the product which was crystallized from ethyl acetate-hexane (14 mg).

EXAMPLE XXVIII

12-Chloro-8,13-epoxy-1α,7β-dihydroxy-labda-5(6),14-diene-11-one 7-acetate

A mixture of the product from Example II (140 mg, 0.309 mmol) in pyridine (2.1 ml) and SOCl$_2$ (0.21 ml) was stirred at room temperature for 20 minutes. Water was added to the mixture and neutralized with 2N HCl. The product was extracted into ethyl acetate and, after work up, was chromatographed on silica TLC plates (1 mm, 10% EtOAc/CHCl$_3$) to give product 20 mg, m.p. 103°–105° C.

EXAMPLE XXIX 8,13-Epoxy-1α,7β,9α-trihydroxy-labda-5(6),14-diene-11-one 7-butyrate A solution of product Example XIIa (44 mg, 0.114 mmol) in pyridine (0.4 ml) and butyric anhydride (0.2 ml) was stirred at 0° C. for 24 hours. H$_2$O was added at 0° C to quench the reaction and the mixture was diluted with EtOAc (200 ml). The organic solution was washed with 0.1N HCl, saturated NaHO$_3$ solution, water and dried (MgSO$_4$). The solvent was evaporated in vacuo to give a residue (45 mg). Purification on silica TLC plates (1 mm, 40% EtOAc-hexane) yielded product 26 mg (0.061 mmol, 54%) which was crystallized from petroleum ether to give m.p. 75°–77° C.

EXAMPLE XXX 8,13-Epoxy-1α,6β,7β,9α-tetrahydroxy-labd-14-en-11-one 6,7-ethylorthoacetate To a solution of 8,13-epoxy-1α,6β,7β,9α-tetrahydroxy-labd-14-en-11-one (800 mg, 0.217 mmol) in dry DMSO (7.05 ml) was added p-toluenesulfonic acid (63.5 mg) and triethylorthoacetate (1.53 ml). The mixture was stirred at room temperature for 2.3 hours, 5% aqueous Na$_2$CO$_3$ (100 ml) was added and the product was extracted with ethyl acetate. The combined EtOAc extracts were washed with water, dried (MgSO$_4$) and evaporated in vacuo to give product (930 mg, 0.272 mmol, 98%). A 100 mg portion of product was crystallized from EtOAc/hexane to give product m.p. 190.5°–193° C.

EXAMPLE XXXI 8,13-Epoxy-1α,9α-dihydroxy-labda-6(7),14-dien-11-one

Forskolin (1 g), p-methoxybenzyl chloride (1.0 ml), potassium iodide (1 g) and potassium carbonate (5 g) in 30 ml dry acetone was heated at 60° C. for 18 hours. After cooling, the precipitate was filtered off, the filtrate evaporated and the residue was separated on a column of silica gel (100 g) eluting with 10% EtOAc/CHCl$_3$ to give 1α-p-methoxybenzyl forskolin (0.4 g) and 0.8 g of a mixture of 1α-p-methoxybenzyl forskolin and 1α-p-methoxybenzyl-6-acetate-7-deacetyl forskolin. This mixture (0.8 g) was treated with MeOH (43.2 ml) and 1.66% NaOH-H$_2$O (10.8 ml) at room temperature overnight. The MeOH was evaporated in vacuo and the residue was dissolved in EtOAc (300 ml), washed with water and dried (MgSO$_4$). Purification on a silica gel column yielded 1α-p-methoxy benzyl-7-deacetyl forskolin (0.63 g). This product was treated with toluene (20 ml), thiocarbonyldiimidazole (765 mg) and N,N-dimethylaminopyridine (63 mg) at 100° C. under a nitrogen atomosphere for 24 hours. After evaporating off the solvent in vacuo, the residue was chromatographed on a column of silica gel (70 g, 20% EtOAc/hexane) to give 1α-p-methoxybenzyl-6β,7β-thiocarbonate 7-deacetyl forskolin (0.59 g). A portion of this product (250 mg) was heated in the presence of 1,3-dimethyl-2-phenyl-1,3-diazo-2-phosphacyclopentane (1.25 ml) at 50° C. under an argon atmosphere in a reacti-vial for 1 day. Chromatography on a silica gel column (300 g, 15% EtOAc/hexane) gave 8,13-epoxy-1α,9α-dihydroxy-labda-6(7),14-diene-11-one 1α-p-methoxy benzyl ether (62 mg). This product was treated with CH$_2$Cl$_2$ : H$_2$O (18:1) (3.0 ml) and DDQ (68.1 mg) at room temperature for 1 day. A further portion of DDQ (25 mg) was added and stirred at room temperature for a further day. The mixture was then filtered through celite, washed with acetone and the product purified on a silica gel columm (50 g, 30% EtOAc/hexane) to give 8,13-epoxy-1α,9α-dihydroxy-labda-6(7),14-diene-11-one 1α-p-methoxybenzoate (60 mg). This product (60 mg) was hydrolyzed with 1.66% NaOH-H$_2$O (0.72 ml) in the presence of MeOH (3.0 ml) for 28 hours at room temperature. The resulting solution was neutralized with 2N HCl and the methanol was removed under reduced pressure. The product was dissolved in EtOAc, washed with water, dried (MgSO$_4$), evaporated in vacuo to a residue and purified on a column of silica gel (100 g, 10% EtOAc/hexane) to give product 40 mg. A 20 mg portion was crystallized from n-hexane, to give product m.p. 92°–93° C.

EXAMPLE XXXII 8,13-Epoxy 1α,9α-dihydroxy-labda-5(6),14-diene-7,11-dione

To a solution of the product from Example XIIa (50 mg) in CHCl$_3$ (3.0 ml) was added activated MnO$_2$ (50 mg, 0.575 mmol). The mixture was stirred at room temperature and additional activated MnO$_2$ (50 mg) was added on each of the following 2 days. On the third day, the mixture was diluted with CHCl$_3$ (100 ml) and filtered through a celite pad which was washed with additional CHCl$_3$ (50 ml). The filtrate was concentrated in vacuo to give a residue 45 mg. Chromatography on a silica gel column (40% EtOAc-CHCl$_3$) yielded product 14 mg (0.04 mmol, 28%). Crystallization from EtOAc/hexane gave product 10 mg, m.p. 205°–208° C.

EXAMPLE XXXIII

14,-E and Z-8,13-epoxy-1α,6β,7β-trihydroxy-labd-14-en-11-one 7-acetate 15-methylcarboxylate A solution of 14,15-dinor-8,13-epoxy-13-formyl-1α,6β,7β-trihydroxy-labdan-11-one 7-acetate (obtained from ozonolysis of 9-deoxyforskolin, 100 mg as in Example XXXIV) in CH$_2$Cl$_2$ was treated with the phosphorane (Ph$_3$P=CH.COOMe; 90 mg). The reaction mixture was stirred at room temperature for 48 hours. The methylene chloride was evaporated in vacuo to provide a gummy residue which was chromatographed on silica gel TLC plates using 40% ethyl acetate/n-hexane as eluent to give the less polar Z-isomer as a colorless amphorphous solid (17.6 mg) and the more polar E-isomer as a colorless amphorphous solid (47.0 mg).

EXAMPLE XXXIV 14,15-Dinor-8,13-epoxy-13-formyl-1α,6β,7β-trihydroxy-labdan-11-one 7-acetate Ozone was passed through a cooled solution (bath temp. −70°) of 9-deoxy forskolin (50 gm) in methylene chloride (4 ml and methanol (3 ml) until the blue coloration persisted. Excess ozone was flushed out with nitrogen followed by addition of 0.1 ml of Me$_2$S. The solution was gradually allowed to warm to room temperature (approx. 45 minutes) after which the solvents were evaporated in vacuo to provide a gummy residue. It was dissolved in CH$_2$Cl$_2$, the solution dried over Na$_2$SO$_4$ and evaporated to dryness. The so obtained aldehyde which was almost pure (TLC; solvent system 20% EtOAc/chloroform) was used as such in the following reactions.

EXAMPLE XXXV

15-Nor-8,13-epoxy-1α,6β,7β-trihydroxy-14-methoximino-labdan-11-one 7-acetate

A solution of 14,15-dinor-8,13-epoxy-13-formyl-1α,6β,7β-trihydroxy-labdan-11-one 7-acetate [as obtained from ozonolysis of 9-deoxy-forskolin, (50 mg) in Example XXXIV] in dry pyridine (2 ml) was treated with NH$_2$OCH$_3$.HCl (12 mg). The mixture was stirred at room temperature for 2 hours after which, the pyridine was removed in vacuo. The resulting solid was distributed between CH$_2$Cl$_2$ and water. After separation of the organic phase, the aqueous phase was extracted once more with CH$_2$Cl$_2$. The combined methylene chloride extracts were dried over Na$_2$SO$_4$ and evaporated to dryness to provide a gummy solid which was subjected to chromatography on silica gel TLC plates using 20% ethyl acetate in chloroform as eluent. Extraction of the major band with ethyl acetate provided the pure title compound as a colorless amorphous solid.

EXAMPLE XXXVI 14,15-Dinor-8,13-epoxy-1α,6β,7β,9α-tetrahydroxy-labd-12-en-11-one 7-acetate 1,9-carbonate A solution of the product from Example IX (0.665 g) in CH$_2$Cl$_2$ (60 ml) was treated with carbonyl diimidazole (0.266 g) for 2 hours at room temperature. The organic solution was washed with H$_2$O, dried (Na$_2$SO$_4$) and evaporated to a solid residue. Purification by preparitive TLC (eluent 20% EtOAc/CHCl$_3$) gave the product (0.45 g.) m.p. 264°-5° C. after crystallization from EtOAc/hexane.

EXAMPLE XXXVII 14,15-Dinor-8,13-epoxy-1α,6β,7β,9α-tetrahydroxy-labd-12-en-11-one A solution of the product from Example XXXVI (0.1 g) in MeOH (8 ml) was treated with 10% NaOH (4 ml) for 15 hours at room temperature. Aqueous oxalic acid was added and the product was extracted into CH$_2$Cl$_2$. The organic solution was washed with water, dried (Na$_2$SO$_4$) and evaporated to give the product (0.094 g).

EXAMPLE XXXVIII 14,15-Dinor-8,13-epoxy-1α,6β,7β,9α-tetrahydroxy-labd-12-en-11-one 7-acetate The product from Example XXXVII (0.06 g) in dry pyridine (0.6 ml) and CH$_2$Cl$_2$ (0.8 ml) was treated with acetic anhydride (0.06 ml) for 20 hours at room temperature. Water was added and after 1 hour the reaction mixture was evaporated to a residue that was purified by preparitive TLC (eluent 20% EtOAc/hexane) to give the product (0.03 g), m.p. 224°-5° C. after crystallization from EtOAc/hexane.

EXAMPLE XXXIX 8,13-Epoxy-1α,6β,7β,trihydroxy-labd-14-en-11-one 6,7-acetonide

The product from Example V (0.1 g) in dry acetone (10 ml) was treated with trimethylsilyl chloride (0.1 ml) at room temperature. After 15 hours a further portion of trimethylsilyl chloride (0.1 ml) was added and after another 15 hours the reaction was diluted with saturated NaHCO$_3$ solution. The product was extracted into CH$_2$Cl$_2$ and the organic extract was washed with H$_2$O, dried (Na$_2$SO$_4$) and evaporated to a residue that was purified by preparitive TLC (eluent 10% EtOAc/CHCl$_3$) to give the product (0.045 g), m.p. 146°-7° C. from EtOAc/hexane.

EXAMPLE XL

13-Epi-14,15-dinor-8,13-epoxy-1α,6β,7β,9α,11-pentahydroxy-labdane 1,9-carbonate 7-acetate The product from Example XXXVI (0.1 g) in EtOH (10 ml) was hydrogenated at 50 psi at room temperature for 36 hours in the presence of PtO$_2$ (0.1 g). The catalyst was then filtered off, the filtrate evaporated to a residue which was purified by preparitive TLC to give the product (0.67 g).

EXAMPLE XLI

13-Epi-14,15-dinor-8,13-epoxy-1α,6β,7β,9α,11-pentahydroxy-labdane 7-acetate

A solution of the product from Example XL (0.067 g) in MeOH (5 ml) was stirred overnight at room temperature with 10% NaOH solution (2 ml). Aqueous oxalic acid was added and the product extracted into CH$_2$Cl$_2$. The organic layer was washed with H$_2$O, dried (Na$_2$SO$_4$) and evaporated to a residue of 13-epi-14,15-dinor-8,13-epoxy-1α,6β,7β,9α,11-pentahydroxy-labdane. This material was dissolved in pyridine (0.7 ml) and CH$_2$Cl$_2$ (0.7 ml) and treated with Ac$_2$O for 20 hours at room temperature. Water was added and the product extracted into CH$_2$Cl$_2$; the organic extract was washed with H$_2$O, dried (Na$_2$SO$_4$) and evaporated to a residue which was purified by preparitive TLC (eluent EtOAc/MeOH/CHCl$_3$-5/1/94) to give the product (0.024 g), m.p. 234°-240° C. from EtOAc/hexane.

We claim:

1. A method for treating allergic reactions in a mammal which comprises administering a bronchodilating effective amount or an amount effective to inhibit histamine release of a compound having structural formula I

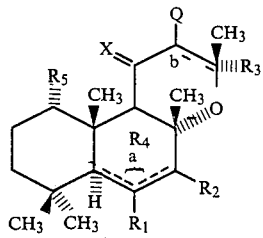

in combination with a pharmaceutically acceptable carrier to said mammal, wherein one of $R_1$ and $R_2$ may be =O and the other of $R_1$ and $R_2$ may be H, or $OR_{11}$ or both of $R_1$ and $R_2$ may be H or $OR_{11}$ wherein $R_{11}$ is H, alkanoyl having from 1 to 6 carbon atoms or

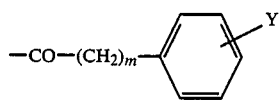

{wherein m is 0, 1, 2 or 3 and Y is hydrogen, halogen, alkyl having from 1 to 6 carbon atoms, alkoxy having from 1 to 6 carbon atoms, alkylthio having from 1 to 6 carbon atoms, OH, $CF_3$, $NO_2$, CN, phenyl, benzyl, phenoxy or $NR_aR_b$ wherein $R_a$ and $R_b$ are the same or different and are H or alkyl having from 1 to 6 carbon atoms}; or
$R_1$ and $R_2$ may be taken together to form

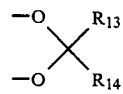

wherein $R_{13}$ and $R_{14}$ may be the same or different and are H, alkyl having from 1 to 6 carbon atoms, alkoxy having from 1 to 6 carbon atoms, alkenyl having from 2 to 6 carbon, alkynyl having from 2 to 6 carbon atoms, or

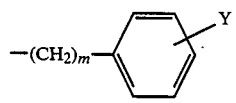

wherein m and Y are as defined above, or
$R_2$ may be $SO_3OR'$ or $OR'$ wherein R' is alkyl having from 1 to 6 carbon atoms;
$R_3$ is hydrogen, alkyl having from 1 to 10 carbon atoms, $CH_2OH$, CHO, $CO_2R_{15}$ {wherein $R_{15}$ is H or alkyl having from 1 to 6 carbon atoms}, —CH=$CR_{16}R_{17}$ {wherein $R_{16}$ is H, halogen, alkyl having from 1 to 6 carbon atoms,

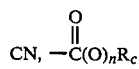

(wherein n is 0 or 1 and $R_c$ is H, alkyl having from 1 to 6 carbon atoms, phenyl or benzyl), $CHOHR_c$ or $C(OR_d)_2R_c$ (wherein $R_c$ is defined above and $R_d$ is alkyl having from 1 to 6 carbon atoms), and $R_{17}$ is H, alkyl having from 1 to 6 carbon atoms, alkoxy having from 1 to 6 carbon atoms, benzyl, phenyl or halogen}, —C≡C—$R_{18}$ {wherein $R_{18}$ is H, alkyl having from 1 to 12 carbon atoms, alkoxy having from 1 to 6 carbon atoms,

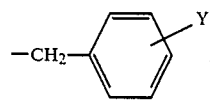

$CO_2Rc$ or

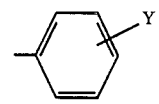

wherein Y and $R_c$ are defined above},
—CHOH—C≡C—$R_{19}$ {wherein $R_{19}$ is H, alkyl of from 1 to 6 carbon atoms, phenyl or benzyl},
—CH=C=$CHR_{19}$ {wherein $R_{19}$ is defined above},
—CH=N—$OR_{19}$ {wherein $R_{19}$ is defined above},

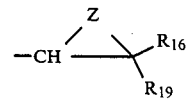

{wherein Z is O or S, and $R_{16}$ and $R_{19}$ are defined above },
—$CH(ZR_{20})_2$ {wherein Z is defined above and $R_{20}$ is alkyl having from 1 to 6 carbon atoms, phenyl, benzyl or the two groups $R_{20}$ may together form —$(CH_2)_p$— wherein p is 2 or 3},

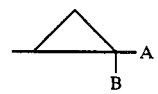

{wherein A and B are H, halogen, alkyl having from 1 to 6 carbon atoms, phenyl, benzyl or

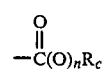

wherein n and $R_c$ are defined above},
—CH=N—NDE {wherein D and E are H, alkyl having from 1 to 6 carbon atoms, benzyl, phenyl, COG, $SO_2G$, $CO_2G$ (wherein G is alkyl having from 1 to 6 carbon atoms, benzyl or phenyl)};
$R_4$ is H or OH;
$R_5$ is OH; or
when $R_4$ and $R_5$ are taken together they may form

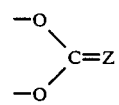

wherein Z is defined above;
a is an optional bond which may be located in either the 5,6 or 6,7 position, such that when a is a 5,6 bond, $R_2$ is =O, H or $OR_{11}$ with $R_{11}$ equal to H, alkanoyl or

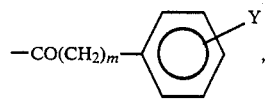

wherein m and Y are as previously defined, such that when $R_2$ is H or $OR_{11}$, $R_1$ is H or $OR_{11}$ with $R_{11}$ equal to alkanoyl or

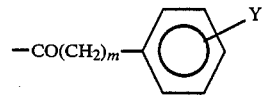

and when $R_2$ is =O, $R_1$ represents H or $OR_{11}$ with $R_{11}$ equal to H, alkanoyl or

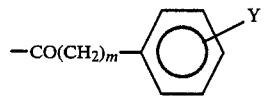

wherein m and Y are as previously defined, and when a is a 6,7 bond, $R_1$ can be H or $OR_{11}$ where $R_{11}$ is alkanoyl, and $R_2$ may be H or $OR_{11}$ where $R_{11}$ is alkanoyl;

b is an optional bond, such that when b is present, Q and $R_3$ are H;

X is O or H/OR" {wherein R" is H, alkanoyl having from 1 to 6 carbon atoms or trifluoroacetyl}; and Q is hydrogen, chlorine or bromine.

2. The method defined in claim 1 wherein $R_1$ and $R_2$ may be the same or different and are hydrogen or $OR_{11}$ wherein $R_{11}$ is defined in claim 1 and Y is hydrogen;

$R_3$ is —CH=CHR$_{30}$ wherein $R_{30}$ is hydrogen, alkyl having from 1 to 6 carbon atoms, phenyl or benzyl;

—C≡CR$_{30}$;

—CHOH—C≡C—R$_{30}$;

—CH=C=CHR$_{30}$;

—CH=N—OR$_{30}$;

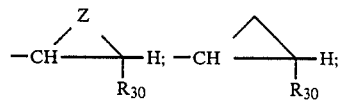

—CH=N—NHR$_{31}$ wherein $R_{31}$ is hydrogen, alkyl having from 1 to 6 carbon atoms, phenyl, benzyl, SO$_2$R$_{32}$ and CO$_2$R$_{32}$ wherein $R_{32}$ is alkyl having from 1 to 6 carbon atoms;

$R_4$ is H or OH;

a is either not present or is located in the 5,6 position in which instance $R_1$ is H and $R_2$ is $OR_{11}$ wherein $R_{11}$ is defined hereinabove;

Y is hydrogen;

X is O or H/OH; and

Q is hydrogen or chlorine.

3. The method defined in claim 1 wherein $R_1$ and $R_2$ may be the same or different and are hydrogen or $OR_{11}$ wherein $R_{11}$ is defined in claim 1 and Y is hydrogen;

$R_3$ is hydrogen, alkyl having from 1 to 6 carbon atoms, —CH=CHR$_{301}$ or —C≡CR$_{301}$ [wherein $R_{301}$ is hydrogen, alkyl having from 1 to 6 carbon atoms, phenyl, benzyl or CO$_2$R$_c$ wherein R$_c$ is defined in claim 1 ];

$R_4$ is H or OH;

R5 is OH;

a is either not present or is located in the 5,6 position in which instance $R_1$ is H and $R_2$ is $OR_{11}$ wherein $R_{11}$ is defined hereinabove;

Y is hydrogen;

X is O or H/OH; and

Q is hydrogen or chlorine.

4. The method defined in claim 3 wherein $R_4$ is H.

5. The method defined in claim 1 which utilizes 7β-acetoxy-8,13-epoxy-1α,6β,9α-trihydroxylabd-14-en-11-one.

6. The method defined in claim 1 which utilizes 8,13-epoxy-1α,6β,7β-trihydroxylabd-14-en-one 7-acetate.

7. The method defined in claim 1 which utilizes 8,13-epoxy-1α,6β,7β,9α-tetrahydroxylabd-14-en-11-one.

8. The method defined in claim 1 which utilizes 6β-acetoxy-8,13-epoxy-1α,7β,9α-trihydroxylabd-14-en-11-one.

9. The method defined in claim 1 which utilizes 8,13-epoxy-1α,7β,9α-trihydroxy-labda-5(6),14-dien-11-one 7-acetate.

* * * * *